United States Patent
Sharp et al.

(10) Patent No.: US 10,388,497 B2
(45) Date of Patent: Aug. 20, 2019

(54) METHOD AND PORTABLE ION MOBILITY SPECTROMETER FOR THE DETECTION OF AN AEROSOL

(71) Applicant: Smiths Detection-Watford Limited, Watford Hertfordshire (GB)

(72) Inventors: David Sharp, Watford Hertfordshire (GB); Alastair Clark, Watford Hertfordshire (GB); William Munro, Watford Hertfordshire (GB); Paul Arnold, Watford Hertfordshire (GB); John FitzGerald, Watford Hertfordshire (GB); David Cutmore, Watford Hertfordshire (GB); Rod Wilson, Watford Hertfordshire (GB)

(73) Assignee: SMITHS DETECTION-WATFORD LIMITED, Hertfordshire (GB)

( * ) Notice: Subject to any disclaimer, the term of this patent is extended or adjusted under 35 U.S.C. 154(b) by 0 days.

(21) Appl. No.: 14/910,931

(22) PCT Filed: Jul. 31, 2014

(86) PCT No.: PCT/GB2014/052356
§ 371 (c)(1),
(2) Date: Feb. 8, 2016

(87) PCT Pub. No.: WO2015/019059
PCT Pub. Date: Feb. 12, 2015

(65) Prior Publication Data
US 2016/0187297 A1 Jun. 30, 2016

(30) Foreign Application Priority Data
Aug. 8, 2013 (GB) .................................. 1314252.6

(51) Int. Cl.
*G01N 27/62* (2006.01)
*H01J 49/00* (2006.01)

(52) U.S. Cl.
CPC .......... *H01J 49/0022* (2013.01); *G01N 27/62* (2013.01); *G01N 27/622* (2013.01); *G01N 27/626* (2013.01); *H01J 49/0013* (2013.01)

(58) Field of Classification Search
CPC ............... H01J 49/0022; H01J 49/0013; H01J 49/0404; G01N 27/626; G01N 27/622; G01N 27/62
See application file for complete search history.

(56) References Cited

U.S. PATENT DOCUMENTS 3,626,180 A 12/1971 Carroll et al.
4,495,414 A * 1/1985 Barrie ................. H01J 49/0422
250/282

(Continued)

FOREIGN PATENT DOCUMENTS

CN 1467498 A 1/2004
CN 201130166 Y 10/2008

(Continued)

OTHER PUBLICATIONS

International Search Report dated Dec. 23, 2014 for Appln. No. PCT/GB2014/052356.

(Continued)

*Primary Examiner* — Brooke Purinton
(74) *Attorney, Agent, or Firm* — Kevin E. West; Advent, LLP

(57) ABSTRACT

A portable ion mobility spectrometry apparatus (1) for detecting an aerosol and a method for using the apparatus. The apparatus comprises an ion mobility spectrometer (3); a portable power source (5) carried by the apparatus for providing power to the apparatus (1); an inlet (7) for (Continued)

collecting a flow of air to be tested by the spectrometer (3); a heater (4) configured to heat the air to be tested to vaporize an aerosol carried by the air and a controller (2) configured to control the spectrometer (3) to obtain samples from the heated air, wherein the controller is configured to increase a heat output from the heater (4) for a selected time period before obtaining samples from the heated air.

15 Claims, 3 Drawing Sheets

(56) References Cited

U.S. PATENT DOCUMENTS

| | | | |
|---|---|---|---|
| 2005/0056780 A1 | 3/2005 | Miller et al. | |
| 2005/0092109 A1* | 5/2005 | Albro | G08B 21/14 73/863.83 |
| 2006/0284102 A1* | 12/2006 | Blanchard | H01J 49/0018 250/423 F |
| 2007/0258861 A1* | 11/2007 | Barket, Jr. | G01N 30/7206 422/89 |
| 2008/0121797 A1* | 5/2008 | Wu | H01J 49/004 250/283 |
| 2011/0266433 A1* | 11/2011 | Jarrell | G01N 30/7206 250/282 |
| 2011/0290041 A1 | 12/2011 | Wang et al. | |
| 2012/0168616 A1 | 7/2012 | Zhang et al. | |
| 2012/0294885 A1* | 11/2012 | David | C07D 471/04 424/193.1 |

FOREIGN PATENT DOCUMENTS

| | | |
|---|---|---|
| CN | 102109434 A | 6/2011 |
| CN | 102565181 A | 7/2012 |
| EP | 0447168 A2 | 9/1991 |
| EP | 2506286 A2 | 10/2012 |
| RU | 2150157 C1 | 5/2000 |
| RU | 2178929 C2 | 1/2002 |
| WO | 2004081527 A2 | 9/2004 |
| WO | 2005036130 A2 | 4/2005 |
| WO | 2005052546 A2 | 6/2006 |
| WO | 2008067395 A2 | 6/2008 |

OTHER PUBLICATIONS

Search Report dated Mar. 24, 2014 for UK Application No. GB1314252. 6.
Combined Search and Examination Report dated Jan. 15, 2015 for UK Application No. GB1413597.4.
Chinese Office Action for Application No. 201480045150.2, dated Jan. 29, 2018.
Japanese Office Action for Application No. 2016-532729, dated May 8, 2018.
Mexican Office Action for Application No. MX/a/2016/001729, dated May 25, 2018.
Russian Office Action and Search Report for 2016105708/28, dated Feb. 6, 2018.

* cited by examiner

Figure 4

```
                    400
                     ↓
        ┌─────────────────────────────────┐
        │ Receive signal to operate       │
        │ spectrometer                    │
        │ 402                             │
        └─────────────────────────────────┘
                     ↓
        ┌─────────────────────────────────┐
        │ Desorb residues from inlet      │
        │ 404                             │
        └─────────────────────────────────┘
                     ↓
        ┌─────────────────────────────────┐
        │ Flush inlet                     │
        │ 406                             │
        └─────────────────────────────────┘
                     ↓
        ┌─────────────────────────────────┐
        │ Draw in sample of air           │
        │ 408                             │
        └─────────────────────────────────┘
                     ↓
        ┌─────────────────────────────────┐
        │ Heat air to vapourise aerosols  │
        │ 410                             │
        └─────────────────────────────────┘
                     ↓
        ┌─────────────────────────────────┐
        │ Sample heated air               │
        │ 412                             │
        └─────────────────────────────────┘
                     ↓
        ┌─────────────────────────────────┐
        │ Perform IMS spectrometry on     │
        │ heated air                      │
        │ 414                             │
        └─────────────────────────────────┘
```

METHOD AND PORTABLE ION MOBILITY SPECTROMETER FOR THE DETECTION OF AN AEROSOL

The present disclosure relates to spectrometry methods and apparatus, and more particularly to ion mobility spectrometry, and to methods and apparatus for applying spectrometry to aerosols.

Some types of ion mobility spectrometers operate by "inhaling" a stream of air, and sampling that air to detect substances of interest. In many cases, ion mobility spectrometers operate by ionising a sample of a gas or vapour, and analysing the resulting ions. To enable the use of ion mobility spectrometers by military and security personnel, hand held, or portable devices have been used. In general these devices are battery powered and it is desired to extend their battery life.

Some analytical apparatus and particularly some ion mobility spectrometers are adapted for the analysis of vapours, and of gases.

Some substances of interest may comprise aerosols. By contrast with a vapour or gas, an aerosol comprises fine particles of solid or liquid suspended in a gas. Where the substance has a low vapour pressure, an ion mobility spectrometer may be unable to detect particles of that substance in an aerosol.

Embodiments of the disclosure will now be described, by way of example only, with reference to the accompanying drawings, in which:

FIG. 4 illustrates a method of operating a spectrometry apparatus.

The present disclosure provides a spectrometer configured to heat a sample of air inhaled into the spectrometer to vapourise aerosols carried by that sample of air before the sample is ionised for analysis. The inhaled sample of air may be heated in the inlet of the spectrometer, in the reaction region in which the sample is ionised, or in a chamber of the spectrometer before the sample is passed into the reaction region. Embodiments of the disclosure are directed to control of the timing of the heating with respect to the operation of the spectrometer to assist sensitivity.

Figure 1:
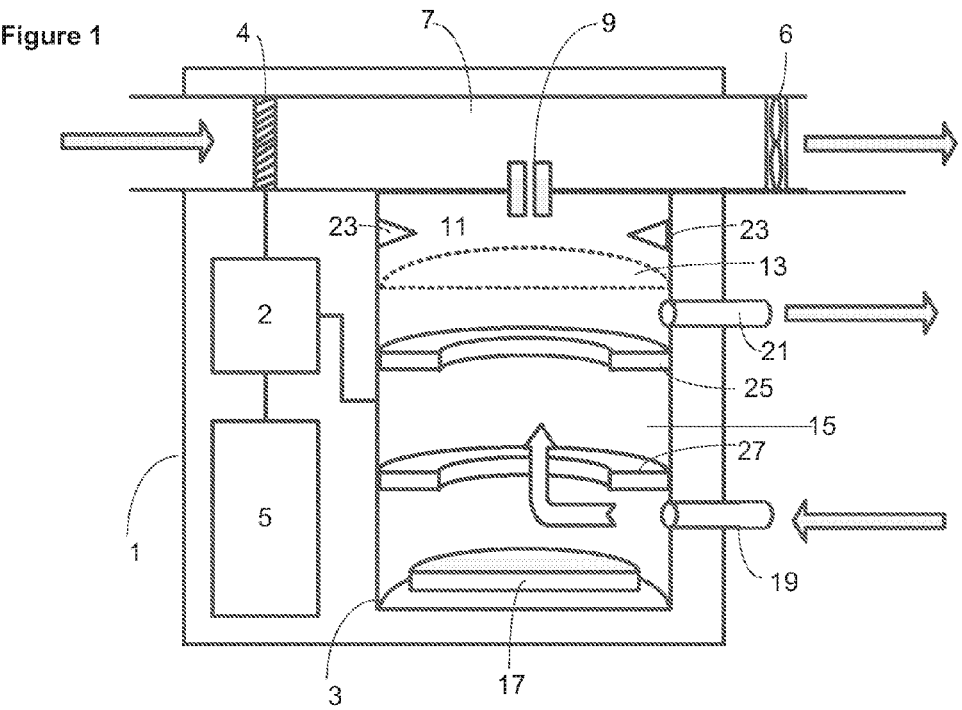
FIG. 1 shows a schematic section view of a portable spectrometry apparatus having a heater arranged to heat air in the inlet of the spectrometer.

FIG. 1 shows an apparatus 1 comprising a spectrometer 3, a portable power source 5 for providing power to the apparatus, an inlet 7, and an air mover 6 for drawing a flow of air through the inlet 7. In the example of FIG. 1, the apparatus 1 comprises a heater 4 configured to heat the air to be tested, and a controller 2 configured to control the air mover 6, the spectrometer 3, and the heater 4.

The inlet 7 comprises a passage through which a flow of air to be sampled by the spectrometer 3 can flow. In the example shown in FIG. 1, the heater 4 comprises a conductive wire heater disposed in the inlet 7 so that air flowing toward the spectrometer flows past the heater 4. As illustrated, the heater 4 is coupled to the controller 2 and coupled to receive a power supply from the power source 5 so that the controller 2 can control operation of the heater 4.

In FIG. 1, the spectrometer 3 comprises an ion mobility spectrometer which is coupled to the inlet 7 by a sampling port 9, and comprises a reaction region 11 in which a sample can be ionised. The sampling port 9 can be operated to obtain a sample from the inlet into the spectrometer. Some examples of sampling ports include 'pinhole' ports and membranes.

A gate electrode 13 may separate the reaction region 11 from a drift chamber 15. The drift chamber 15 comprises a detector 17 toward the opposite end of the drift chamber 15 from the gate electrode 13. The drift chamber 15 also comprises a drift gas inlet 19, and a drift gas outlet 21 arranged to provide a flow of drift gas along the drift chamber 15 from the detector 17 towards the gate 13.

The sampling port 9 can be operated to sample air from the inlet 7 into the reaction region 11 of the spectrometer 3. The reaction region 11 comprises an ioniser 23 for ionising a sample. In the example shown in FIG. 1 the ioniser 23 comprises a corona discharge ioniser comprising electrodes.

The drift chamber 15 also comprises drift electrodes 25, 27, for applying an electric field along the drift chamber 15 to accelerate ions towards the detector 17 against the flow of the drift gas.

In operation, in response to the spectrometer 3 being activated by an operator, the controller 2 operates the air mover 6 so that a flow of air is drawn through the inlet 7.

To desorb residues which may have accumulated on the inlet 7 or heater 4, the controller 2 increases the heat output from the heater 4 whilst the air mover 6 is drawing air through the inlet 7 to desorb substances from the heater 4 and remove them from the inlet 7. To desorb such residues, the heater 4 may be heated to a temperature of at least 150° C. The flow of air through the inlet 7 flushes the desorbed substances out of the inlet 7 in preparation for testing a sample of air.

In this process of desorbing residues, the controller 2 is configured to increase the heat output from the heater 4 for a selected time period before sampling the flow of air with the spectrometer 3. This time period may be selected based on the temperature of the heater 4 during the desorption, the type of aerosols which are to be detected, and/or based on the type of residues expected in the inlet. Increasing the heat output from the heater may comprise increasing the power provided to the heater, and may comprise switching the heater on.

After the selected time period has elapsed, whilst the air mover 6 continues to draw air past the heater 4, the controller 2 controls the spectrometer sampling port 9 to obtain a sample from the heated flow of air in the inlet 7. The controller 2 then controls the spectrometer 3 to perform ion mobility spectrometry on the heated sample in the reaction region 11.

In some embodiments the controller 2 is configured to reduce the temperature of the heater after the selected time period, and prior to sampling the flow of air with the spectrometer. In some embodiments, the controller 2 may reduce the power provided to the heater 4 prior to obtaining samples so that the air to be sampled is heated by the residual heat from desorbing residues from the inlet. In some examples reducing the power may comprise reducing the heat output from the heater 4, and may comprise switching the heater 4 off.

In an embodiment, the controller 2 controls the heater 4 to provide a first heat output for the selected time period (for desorption of residues) prior to obtaining samples. The controller 2 may then control the heater 4 to provide a second heat output to vapourise aerosols carried by the flow of air, and control the sampling port 9 to obtain samples of the vapourised aerosols from the heated flow of air. The controller 2 may be configured so the samples are obtained while the heater 4 is controlled to provide the second heat output, or while the heater 4 is cooling.

In an embodiment, the controller 2 is configured to control the sampling port 9 to obtain at least one initial sample from the inlet during the selected time period, and to analyse the initial sample to test for the presence of residues. Based on this test, the controller 2 may extend or shorten the selected time period. For example, in the event that the controller determines from this test that residues have been desorbed and removed from the inlet, the controller may control the heater 4 to provide the second heat output to vapourise aerosols, and control the sampling port 9 to obtain samples of the vapourised aerosols. In this embodiment, the inlet may be controllable to circulate a flow of air from the inlet, into a filter, such as a charcoal pack, and then recirculate it back through the inlet whilst applying the first, higher, heat output. The controller 2 may be configured to test the recirculated air flow until it is determined that residues have been desorbed from the inlet.

The first heat output may be selected to provide a temperature of at least 150° C. In an embodiment the second heat output is less than the first heat output. Controlling the heater to provide the second heat output may comprise reducing the power provided to the heater 4, for example by switching it off.

The heater 4 may be disposed around or in the inlet. The heater may comprise a conductor, such as a wire which may be arranged to be heated by resistive heating. The wire may comprise metal. The heater 4 may be arranged as a grid or mesh to provide an obstacle in the inlet so that the flow of air through the inlet flows through or around the heater. In one example the heater comprises a knitted structure, such as a wad or tangle of wire. One example of such a structure comprises a knitted mesh of wire such as Knitmesh®.

The grid or mesh structure may be arranged so that the wire occupies less than 80% of its volume, in some examples less than 60%, in some examples less than 40%, in some examples less than 20% of the volume is occupied by wire, and the remaining volume may be occupied by air spaces through which air to be heated can flow. In an embodiment the structure is at least 60% air by volume, and in some embodiments the structure is approximately 70% air by volume. The use of lower densities has been found to improve the efficiency of the apparatus, and the sensitivity achieved by heating the airflow in the spectrometer.

Where a knitted or tangled wire structure, such as Knitmesh®, is used, the heater 4 may be wrapped around the outside of the structure. In some embodiments the knitted or tangled wire structure may be heated by passing a current through the structure.

The heater 4 may provide a constriction in the inlet 7, or it may be arranged around a constriction in the path of the flow of air into the reaction region, such as at the sampling port 9 of the spectrometer 3. In an embodiment the port 9 may be heated, or a heater, such as a resistive filament heater of the kind that might be found in a filament bulb, may be disposed in the flow of air upstream of the port 9.

In some examples the heater 4 may comprise an infra-red source, such as an infra-red lamp or LED, or an infra-red laser. In some examples the heater 4 may comprise a jet, or a plurality of jets, of hot air injected into the flow of air in the inlet 7 before the flow of air reaches the sampling port 9 of the spectrometer 3.

Figure 2:
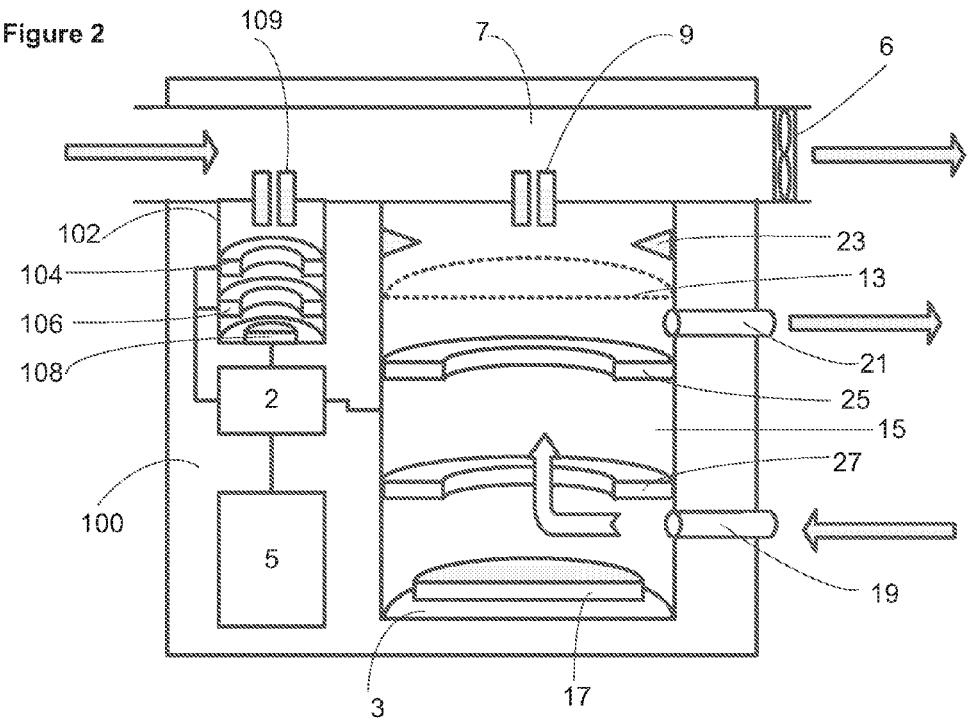
FIG. 2 shows a schematic section view of a portable spectrometry apparatus having a chamber in which air can be captured and heated.

FIG. 2 shows a second apparatus 100. The apparatus shown in FIG. 2 provides an alternative way to perform ion mobility spectrometry to analyse aerosols with low vapour pressure. Rather than heating the flow of air as it passes into the inlet, the apparatus 100 illustrated in FIG. 2 is configured to draw air into a chamber 102, and to heat the air in the chamber 102 to vapourise aerosols. The heated air can then be provided back into the flow of air in the inlet 7 to be sampled by the spectrometer 3.

The apparatus 100 shown in FIG. 2 comprises a spectrometer 3, a portable power source 5 for providing power to the apparatus 100, an inlet 7, and an air mover 6 for drawing a flow of air through the inlet 7. As in the example shown in FIG. 1, the spectrometer 3 of FIG. 2 is coupled to the inlet 7 by a sampling port 9 so that the spectrometer 3 can obtain a sample of air from the inlet 7.

The apparatus shown in FIG. 2 also comprises a chamber 102 coupled to the inlet 7 by a port 109 upstream of the sampling port 9 of the spectrometer so that air flowing through the inlet 7 passes the chamber port 109 before passing the spectrometer sampling port 9.

The chamber 102 comprises two electrodes 104, 106, and a pump 108. The pump 108 is adapted to draw air from the inlet 7 through the port 109 into the chamber 102, and to expel air from the chamber 102 back into the inlet 7. The electrodes 104, 106 are adapted for applying an electric charge to particles of an aerosol in the chamber 102. The electrodes 104, 106 may also be adapted for heating the charged particles.

In operation of the apparatus of FIG. 2, in response to the spectrometer 3 being activated by an operator, the controller 2 operates the air mover 6 so that a flow of air is drawn through the inlet 7. The controller 2 then operates the pump 108 to draw air from the inlet 7 into the chamber. The controller 2 then operates the electrodes 104, 106 to apply an electric charge to aerosol particles in the sample in the chamber 102.

Once the aerosol particles have been charged, the controller 2 operates the electrodes 104, 106 to apply an alternating electric field, such as a radio frequency electric field, between the electrodes 104, 106 to raise the temperature of the charged aerosol. This avoids the need to provide resistive heating. The controller 2 then operates the pump 108 to expel the vapour back into the inlet 7, so that the flow of air in the inlet 7 carries the vapour to the sampling port 9 to be sampled and analysed by the spectrometer 3.

Although in the example described above, the same electrodes 104, 106 are used for both charging and heating the aerosol, other configurations are contemplated. For example a ground reference electrode may be provided, whilst a first electrode 104 may be used to charge the aerosol, and the second electrode 106 may apply an electric field that alternates with respect to ground. In other examples four electrodes may be used, a first two of these may be used for charging the aerosol, and a second two electrodes may be used for applying the alternating electric field to heat the aerosol.

In some examples, the chamber 102 of FIG. 2 may comprise a heater (such as a heater similar to the heater 4 shown in FIG. 1). In these examples, once the aerosol particles have been charged, the controller 2 can control the electrodes 104, 106 to apply an electric field that draws the charged aerosol particles onto one, or both of, the electrodes 104, 106. Once the charged aerosol particles have been captured in this way, the controller 2 can operate the heater to vapourise the captured particles.

The heater may comprise a resistive heater, an infra-red lamp, laser, LED, a jet of heated air, or any other heat source arranged for heating captured aerosol particles on the electrode. In some possibilities, one or both of the electrodes 104, 106, may be configured so that a current may be passed through the electrode to provide resistive heating of the electrode.

In some examples, the chamber 102 need not comprise any electrodes, and may simply comprise a heater. In these examples, air is drawn into the chamber to be heated, and heated by the heater before being released back into the flow of air in the inlet 7 to be analysed by the spectrometer 3.

Although the chamber 102 is described as comprising a pump, any device for moving air into and out of the chamber 102 may be used, for example a fan may be used to draw air into and out from the chamber 102, or a piston may be used to vary the volume of the chamber 102 to draw air in, and push air out of the chamber 102 through the port 109 to the inlet 7.

In some examples the chamber 102 may be provided in the inlet 7. For example instead of drawing some air from the inlet into a separate chamber 102 to be heated, the chamber 102 may be part of the inlet, and the electrodes 104, 106 may be provided in the inlet 7. Accordingly, the electrodes 104, 106 may be operated to charge and heat aerosols in the inlet as described above with reference to operation of the chamber 102.

Figure 3:
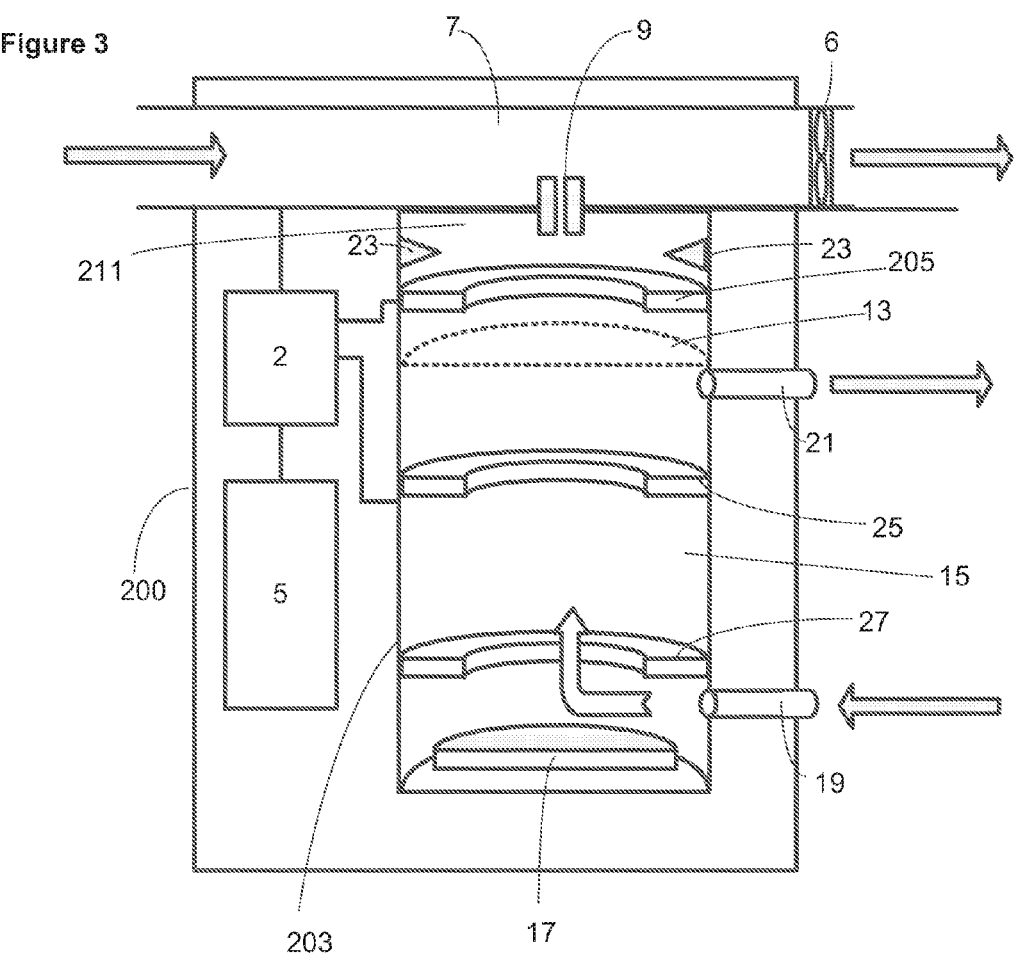
FIG. 3 shows a schematic section view of another apparatus in which a sample of air can be heated in the reaction region of an ion mobility spectrometer.

FIG. 3 shows a third apparatus 200. The apparatus 200 shown in FIG. 3 provides another alternative solution to enable the use of ion mobility spectrometry to analyse aerosols with low vapour pressure. In the example of FIG. 3, the reaction region 211 of the spectrometer 203 comprises a heater 205 for heating a sample of air to vapourise aerosols before the sample is ionised.

The apparatus 200 shown in FIG. 3 comprises a spectrometer 203, an inlet 7, a controller 2, and a portable power source 5 for providing power to the apparatus 200.

The inlet 7 comprises an air mover 6 for drawing a flow of air through the inlet 7.

The spectrometer 203 of FIG. 3 comprises a sampling port 9 coupled to the inlet 7 for obtaining a sample of air from the inlet 7, and a reaction region 211 in which a sample can be ionised. As illustrated in FIG. 3, the reaction region comprises an ioniser 23, and a heater 205 coupled to be controlled by the controller 2. A gate electrode 13 may separate the reaction region 211 from a drift chamber 15.

The drift chamber 15 comprises a detector 17 toward the opposite end of the drift chamber 15 from the gate electrode 13. The drift chamber 15 also comprises a drift gas inlet 19, and a drift gas outlet 21 arranged to provide a flow of drift gas along the drift chamber 15 from the detector 17 towards the gate 13.

The drift chamber also comprises electrodes 25, 27 for applying an electric field to accelerate ions towards the detector against the flow of drift gas.

In operation of the apparatus of FIG. 3, in response to the spectrometer 203 being activated by an operator, the controller 2 operates the air mover 6 so that a flow of air is drawn through the inlet 7. The controller 2 then operates the spectrometer 3 to obtain a sample of air from the inlet 7 through the port 9 into the reaction region 211.

With a sample of air in the reaction region 211, the controller 2 operates the heater 205 to heat the sample to vapourise aerosols in situ in the reaction region 211. Once the sample has been heated, the controller 2 operates the ioniser 23 to ionise the sample for analysis by the spectrometer.

In some possibilities the ioniser 23 may comprise the heater. For example, where the ioniser comprises a corona discharge ioniser, the electrodes of the ioniser may be heated to raise the temperature of the sample in the reaction region 211. In some possibilities the electrodes of the ioniser 23 may be configured to operate as the electrodes 104, 106 described above with reference to FIG. 2. For example, the controller 2 may be configured to control the ioniser 23 to apply an electric charge to aerosol particles in the reaction region, and to raise the temperature of the charged particles by applying an alternating electric field, for example a radio frequency electric field. In some possibilities, the controller 2 may be configured to control the ioniser 23 to apply an electric charge to aerosol particles in the reaction region 211, and to apply an electric field to attract the charged particles onto an electrode before heating the particles on the electrode. These possibilities may use the electrodes of the ioniser 23, or separate electrodes may be provided for the purpose.

In the various apparatuses 1, 100, 200 described with reference to FIG. 1, FIG. 2, and FIG. 3, the portable power source 5 may comprise a battery, a fuel cell, a capacitor, or any other portable source of electrical power suitable for providing electrical power to the apparatus.

The apparatuses 1, 100, 200 shown in the drawings are described as comprising an air mover 6. This air mover may for example be provided by a pump, or a fan or any device suitable for drawing a flow of air through the inlet, such as bellows. Where such a device is used it need not be part of the apparatus, and may be provided separately.

The apparatuses 1, 100, 200 shown in the drawings comprise a single mode spectrometer 3, 203. However, in some possibilities the spectrometer 3, 203 may comprise a positive mode spectrometer 3, and a negative mode spectrometer 3. In some possibilities a single spectrometer may be switchable between positive and negative mode operation.

The controller 2 described with reference to FIG. 1, FIG. 2, and FIG. 3 may be provided by digital logic, such as field programmable gate arrays, FPGA, application specific integrated circuits, ASIC, a digital signal processor, DSP, or by software loaded into a programmable processor. Aspects of the disclosure comprise computer program products, and may be recorded on non-transitory computer readable media, and these may be operable to program a processor to perform any one or more of the methods described herein.

Whilst the apparatuses shown in FIG. 1, FIG. 2, and FIG. 3 provide embodiments of the present disclosure, other embodiments are contemplated.

FIG. 4 illustrates a method 400 of controlling power consumption in a spectrometer for analysing aerosols. As illustrated in FIG. 4 the method comprises receiving 402 a signal to operate the spectrometer. In response to the signal, an air mover can be activated to draw a flow of air through the spectrometer inlet. The inlet can then be heated so that residues can be desorbed 404 from the spectrometer, and flushed 406 out of the inlet by the air mover. After desorbing and flushing out the residues, air to be tested for aerosols is drawn 408 into an inlet of the spectrometer.

The air is heated 410 to vapourise an aerosol carried by the air, and a sample is obtained 412 from the heated air. The sample can then be analysed 414 with the spectrometer.

To conserve energy, heating may be stopped prior to obtaining a sample from the heated air. The samples may be obtained 412 whilst the residual heat from desorbing 404 residues continues to heat the air.

The heating may comprise heating an inlet of the spectrometer, and this heating may be done without obtaining samples for analysis to ensure that residues are desorbed, and removed, from the inlet before sampling. In some possibilities, residues may be desorbed from the spectrometer after a sample has been obtained, and in these and other possibilities, it may not be necessary to desorb residues before obtaining samples. Heating may comprise heating air in a reservoir, and then releasing the heated air from the reservoir into an inlet of the spectrometer. Heating may also comprise heating air in a reaction region of the spectrometer.

Although embodiments of the disclosure have been described as having particular application in ion mobility spectrometers, the apparatus and methods described may be applied in other analysis systems where there is a need to test for vapours associated with aerosols having a low vapour pressure.

As will be appreciated a vapour may comprise a substance in its gaseous phase at a temperature lower than its critical point. By contrast with a vapour or gas, an aerosol comprises fine particles of solid or liquid suspended in a gas. As used herein, the term "vapourise" is used to mean converting at least some of a substance from a solid or liquid to a vapour or a gas.

Apparatus features described herein may be provided as method features, and vice versa.

In a first aspect there is provided a portable spectrometry apparatus for detecting an aerosol. The apparatus of this first aspect may comprise a spectrometer; a portable power source carried by the apparatus for providing power to the apparatus; an inlet for collecting a flow of air to be tested by the spectrometer; a heater configured to heat the air to be tested to vapourise an aerosol carried by the air; a controller configured to control the spectrometer to obtain samples from the heated air, wherein the controller is configured to increase a heat output from the heater for a selected time period before obtaining samples from the heated air. In an embodiment, increasing the heat output includes increasing the heat output from zero, for example increasing the heat output may include switching the heater on. In an embodiment increasing the heat output includes increasing the heat output from an initial non-zero heat output.

In this first aspect the time period can be selected to enable substances desorbed from the inlet to leave the inlet, and the controller can be configured to reduce the power provided to the heater before obtaining the samples. For example the controller may be configured to reduce the heat output from the heater after the selected time period, and to obtain the samples while the heater is cooling, for example before the heater has returned to ambient temperature.

In some examples of this first aspect, the inlet comprises a constriction adapted to reduce the cross section of the inlet through which the flow of air can pass, and the heater is arranged to heat the constriction more than the rest of the inlet. This constriction may comprise the heater. Heaters in this first aspect may comprise wire arranged in the path of the flow of air so that the flow of air must pass the wire to reach the spectrometer. For example, the heater can comprise at least one of a grid, a mesh, and a tangled or knitted structure.

In a second aspect there is provided a spectrometry apparatus for identifying an aerosol. In this second aspect the apparatus comprises: a spectrometer; a chamber for holding a sample of air; and a heater configured to heat an aerosol carried by the sample of air to vapourise the aerosol in the chamber, wherein the spectrometer is adapted to identify the aerosol based on analysing the vapourised aerosol.

The chamber of this second aspect may comprise an ioniser for ionising a sample of air in the chamber, and the apparatus may comprise a controller configured to operate the heater before operating the ioniser to ionise the sample of air. The chamber of this second aspect may comprise an electrode configured to apply an electric charge to an aerosol in the chamber.

In a third aspect there is provided a method of controlling power consumption in a spectrometer for analysing aerosols. In this third aspect the method comprises increasing a heat output from a heater for desorbing substances from an inlet of the spectrometer; after desorption, drawing air to be tested for aerosols into an inlet of the spectrometer; heating the air to vapourise an aerosol carried by the air; obtaining a sample from the heated air; and analysing the vapourised aerosol with the spectrometer. Increasing the heat output may comprise increasing the power provided to the heater, for example by switching the heater on.

The method of this third aspect may comprise reducing a heat output from the heater prior to obtaining a sample from the heated air. In the third aspect, heating the air may comprise heating an inlet of the spectrometer. This may comprise heating the inlet without obtaining samples to desorb substances from the inlet, and may comprise removing the desorbed substances from the inlet before obtaining samples.

In an embodiment heating the air comprises heating air in a chamber, and then releasing the heated air from the chamber to be sampled from an inlet of the spectrometer. In an embodiment heating the air comprises heating the air in a chamber of the spectrometer, for example heating in a reaction region. In an embodiment the chamber comprises a corona discharge ioniser for ionising a sample in the chamber, and the method comprises heating the corona discharge ioniser prior to ionising the sample. In an embodiment the method comprises applying an electric charge to an aerosol (for example in the chamber) and heating the charged aerosol by subjecting the charged aerosol to an alternating electric field.

It should also be appreciated that particular combinations of the various features described and defined in any aspects of the invention can be implemented and/or supplied and/or used independently. Other examples and variations will be apparent to the skilled addressee in the context of the present disclosure.

The invention claimed is:

1. A portable spectrometry apparatus for detecting an aerosol, the apparatus comprising:
    a spectrometer for detecting ions;
    a portable power source carried by the apparatus for providing power to the apparatus;
    an inlet for collecting a flow of air to be tested by the spectrometer;
    a heater configured to heat the air to be tested to vapourise an aerosol carried by the air, the heater comprising wire arranged in the path of the flow of air so that the flow of air passes the wire to reach the spectrometer;
    a controller configured to control the spectrometer to obtain samples from the heated air, wherein the controller is configured to increase a heat output from the heater for a selected time period before obtaining samples from the heated air.

2. The apparatus of claim 1 wherein the time period is selected to enable substances desorbed from the inlet to leave the inlet.

3. The apparatus of claim 1 in which the controller is configured to reduce a power provided to the heater after the selected time period, and to obtain the samples after reducing the power.

4. The apparatus of claim 1 in which the inlet comprises a constriction adapted to reduce the cross section of the inlet through which the flow of air can pass, and the heater is arranged to heat the constriction more than the rest of the inlet.

5. The apparatus of claim 4 in which the constriction comprises the heater.

6. The apparatus of claim 4 in which the heater comprises at least one of a grid, a mesh, and a tangled or knitted structure.

7. The apparatus of claim 1 comprising a chamber for holding a sample of air to be tested, wherein the heater is configured to heat air in the chamber.

8. The apparatus of claim 7 in which the controller is arranged to release the heated air from the chamber into the flow of air in the inlet to provide a heated flow, and to control the spectrometer to obtain samples from the heated flow.

9. The apparatus of claim 1 wherein the spectrometer is an ion mobility spectrometer.

10. A method of controlling power consumption in a spectrometer for analysing aerosols and detecting ions, the method comprising:
  receiving a signal to operate the spectrometer;
  in response to the signal, increasing a heat output from a heater for desorbing substances from an inlet of the spectrometer;
  after desorption, drawing a flow of air to be tested for aerosols into an inlet of the spectrometer;
  heating the flow of air to vapourise an aerosol carried by the air, the heater for heating the flow of air comprising wire arranged in the path of the flow of air so that the flow of air passes the wire to reach the spectrometer;
  obtaining a sample from the heated air; and
  analysing the vapourised aerosol with the spectrometer.

11. The method of claim 10 further comprising reducing power provided to the heater prior to obtaining a sample from the heated air.

12. The method of claim 10 in which heating the air comprises heating an inlet of the spectrometer.

13. The method of claim 12 in which heating the inlet of the spectrometer comprises heating the inlet without obtaining samples.

14. The method of claim 10 comprising removing the desorbed substances from the spectrometer before obtaining the sample.

15. The apparatus of claim 10 wherein the spectrometer is an ion mobility spectrometer.

* * * * *